United States Patent
Chan et al.

(10) Patent No.: US 7,468,051 B2
(45) Date of Patent: Dec. 23, 2008

(54) OCCLUSION BALLOON CATHETER WITH EXTERNAL INFLATION LUMEN

(75) Inventors: Huey Quoc Chan, San Jose, CA (US); Stephen Griffin, San Jose, CA (US); Elaine Lim, Fremont, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 517 days.

(21) Appl. No.: 10/791,008

(22) Filed: Mar. 2, 2004

(65) Prior Publication Data
US 2005/0197667 A1 Sep. 8, 2005

(51) Int. Cl.
*A61M 29/00* (2006.01)

(52) U.S. Cl. .................... 604/96.01; 606/194

(58) Field of Classification Search ............. 604/96.01, 604/509, 524, 527, 103.01–103.14, 525, 604/103, 99.01–99.04, 97.01–97.02, 98.01–98.02; 606/194
See application file for complete search history.

(56) References Cited

U.S. PATENT DOCUMENTS

| | | |
|---|---|---|
| 3,190,291 A | 6/1965 | Foley |
| 3,331,371 A | 7/1967 | Rocchi et al. |
| 3,378,011 A | 4/1968 | Vitello |
| 3,379,197 A | 4/1968 | Hayes |
| 3,402,717 A | 9/1968 | Doherty |
| 3,402,718 A | 9/1968 | Doherty |
| 3,417,750 A | 12/1968 | Carson |
| 3,527,226 A | 9/1970 | Hakim |
| 3,602,226 A | 8/1971 | Ericson |
| 3,675,658 A | 7/1972 | Taylor |
| 3,726,283 A | 4/1973 | Dye et al. |
| 3,742,960 A | 7/1973 | Dye et al. |
| 3,985,139 A | 10/1976 | Penar |
| 4,318,410 A | 3/1982 | Chin |
| 4,323,071 A | 4/1982 | Simpson et al. |
| 4,411,055 A | 10/1983 | Simpson et al. |
| 4,413,989 A | 11/1983 | Schjeldahl et al. |
| 4,490,421 A | 12/1984 | Levy |
| 4,545,367 A | 10/1985 | Tucci |
| 4,549,879 A | 10/1985 | Groshong et al. |
| 4,564,014 A | 1/1986 | Fogarty et al. |
| 4,573,966 A | 3/1986 | Weikl et al. |
| 4,582,181 A | 4/1986 | Samson |
| 4,597,755 A | 7/1986 | Samson et al. |
| 4,606,347 A | 8/1986 | Fogarty et al. |
| 4,684,363 A | 8/1987 | Ari et al. |
| 4,715,378 A | 12/1987 | Pope, Jr. et al. |

(Continued)

FOREIGN PATENT DOCUMENTS

DE 36 25 871 A1 2/1988

(Continued)

*Primary Examiner*—Nicholas D Lucchesi
*Assistant Examiner*—Theodore J Stigell
(74) *Attorney, Agent, or Firm*—Crompton, Seager & Tufte, LLC (57) ABSTRACT

Catheters such as guide catheters can be configured to provide distal occlusion, while still providing sufficient interior lumen space for device delivery. Such catheters can also provide a desired level of flexibility, yet can include sufficient column support. A catheter can include an elongate shaft with a lumen, an inflatable compliant balloon disposed over the distal region of the shaft, and an external inflation component.

6 Claims, 4 Drawing Sheets

U.S. PATENT DOCUMENTS

| | | | |
|---|---|---|---|
| 4,748,982 A | 6/1988 | Horzewski et al. | |
| 4,762,129 A | 8/1988 | Bonzel | |
| 4,775,371 A | 10/1988 | Mueller, Jr. | |
| 4,779,611 A | 10/1988 | Grooters et al. | |
| 4,793,351 A | 12/1988 | Landman et al. | |
| 4,796,629 A | 1/1989 | Grayzel | |
| 4,811,737 A | 3/1989 | Rydell | |
| 4,813,934 A | 3/1989 | Engelson et al. | |
| 4,848,344 A | 7/1989 | Sos et al. | |
| 4,863,440 A | 9/1989 | Chin | |
| 4,906,244 A | 3/1990 | Pinchuck et al. | |
| 4,930,341 A | 6/1990 | Euteneuer | |
| 4,932,959 A | 6/1990 | Horzewski et al. | |
| 4,943,278 A | 7/1990 | Euteneuer et al. | |
| 4,998,923 A | 3/1991 | Samson et al. | |
| 5,027,812 A * | 7/1991 | Shapiro et al. | 128/207.18 |
| 5,035,705 A | 7/1991 | Burns | |
| 5,100,385 A | 3/1992 | Bromander | |
| 5,114,398 A | 5/1992 | Trick et al. | |
| 5,141,518 A | 8/1992 | Hess et al. | |
| 5,180,364 A | 1/1993 | Ginsburg | |
| 5,180,367 A | 1/1993 | Kontos et al. | |
| 5,195,971 A | 3/1993 | Sirhan | |
| 5,209,728 A | 5/1993 | Kraus et al. | |
| 5,209,728 A | 5/1993 | Kraus et al. | |
| 5,217,434 A | 6/1993 | Arney | |
| 5,224,933 A | 7/1993 | Bromander | |
| 5,238,004 A | 8/1993 | Sahatjian et al. | |
| 5,246,420 A | 9/1993 | Kraus et al. | |
| 5,306,247 A * | 4/1994 | Pfenninger | 604/102.02 |
| 5,324,263 A | 6/1994 | Kraus et al. | |
| 5,334,153 A | 8/1994 | McIntyre et al. | |
| 5,338,301 A | 8/1994 | Diaz | |
| 5,378,238 A | 1/1995 | Peters et al. | |
| 5,395,334 A * | 3/1995 | Keith et al. | 604/103.09 |
| 5,413,557 A | 5/1995 | Solar | |
| 5,421,826 A | 6/1995 | Crocker et al. | |
| 5,423,742 A | 6/1995 | Theron | |
| 5,443,457 A | 8/1995 | Ginn et al. | |
| 5,449,371 A | 9/1995 | Pinchuk et al. | |
| RE35,176 E | 3/1996 | Powell | |
| 5,496,275 A | 3/1996 | Sirhan et al. | |
| 5,527,292 A * | 6/1996 | Adams et al. | 604/171 |
| 5,554,118 A | 9/1996 | Jang | |
| 5,609,606 A * | 3/1997 | O'Boyle | 606/194 |
| 5,611,807 A * | 3/1997 | O'Boyle | 606/169 |
| 5,695,468 A | 12/1997 | Lafontaine et al. | |
| 5,728,063 A | 3/1998 | Preissman et al. | |
| 5,728,065 A | 3/1998 | Follmer et al. | |
| 5,728,066 A * | 3/1998 | Daneshvar | 604/96.01 |
| 5,743,875 A | 4/1998 | Sirhan et al. | |
| 5,752,934 A | 5/1998 | Campbell et al. | |
| 5,769,819 A | 6/1998 | Schwab et al. | |
| 5,772,642 A | 6/1998 | Ciamacco, Jr. et al. | |
| 5,776,099 A | 7/1998 | Tremulis | |
| 5,785,685 A | 7/1998 | Kugler et al. | |
| 5,797,948 A | 8/1998 | Dunham | |
| 5,807,328 A | 9/1998 | Briscoe | |
| 5,814,016 A | 9/1998 | Valley et al. | |
| 5,836,924 A | 11/1998 | Kelliher et al. | |
| 5,868,705 A | 2/1999 | Bagaoisan et al. | |
| 5,868,706 A * | 2/1999 | Cox | 604/96.01 |
| 5,916,194 A | 6/1999 | Jacobsen et al. | |
| 5,921,957 A * | 7/1999 | Killion et al. | 604/96.01 |
| 6,017,323 A | 1/2000 | Chee | |
| 6,024,693 A * | 2/2000 | Schock et al. | 600/18 |
| 6,030,405 A * | 2/2000 | Zarbatany et al. | 606/191 |
| 6,045,531 A | 4/2000 | Davis | |
| 6,071,273 A | 6/2000 | Euteneuer et al. | |
| 6,102,931 A | 8/2000 | Thornton | |
| 6,110,142 A | 8/2000 | Pinchuk et al. | |
| 6,117,106 A * | 9/2000 | Wasicek et al. | 604/96.01 |
| 6,129,707 A * | 10/2000 | Cryer | 604/96.01 |
| 6,136,258 A | 10/2000 | Wang et al. | |
| 6,143,015 A | 11/2000 | Nobles | |
| 6,146,357 A | 11/2000 | Addis | |
| 6,176,843 B1 | 1/2001 | DiCaprio et al. | |
| 6,186,978 B1 * | 2/2001 | Samson et al. | 604/96.01 |
| 6,190,304 B1 | 2/2001 | Downey et al. | |
| 6,217,547 B1 * | 4/2001 | Lee | 604/96.01 |
| 6,248,121 B1 | 6/2001 | Nobles | |
| 6,270,477 B1 | 8/2001 | Bagaoisan et al. | |
| 6,315,757 B1 | 11/2001 | Chee et al. | |
| 6,395,208 B1 | 5/2002 | Herweck et al. | |
| 6,425,908 B2 | 7/2002 | Ravenscroft et al. | |
| 6,508,803 B1 | 1/2003 | Horikawa et al. | |
| 6,517,515 B1 * | 2/2003 | Eidenschink | 604/101.05 |
| 6,554,795 B2 | 4/2003 | Bagaoisan et al. | |
| 6,565,527 B1 | 5/2003 | Jonkman et al. | |
| 6,599,266 B2 | 7/2003 | Morse et al. | |
| 6,612,999 B2 | 9/2003 | Brennan et al. | |
| 6,638,245 B2 | 10/2003 | Miller et al. | |
| 6,893,417 B2 * | 5/2005 | Gribbons et al. | 604/103.04 |
| 6,905,477 B2 * | 6/2005 | McDonnell et al. | 604/103.04 |
| 6,960,186 B1 * | 11/2005 | Fukaya et al. | 604/103.06 |
| 2002/0128598 A1 | 9/2002 | Nobles | |
| 2004/0143240 A1 * | 7/2004 | Armstrong et al. | 604/528 |
| 2004/0254528 A1 * | 12/2004 | Adams et al. | 604/96.01 |

FOREIGN PATENT DOCUMENTS

| | | |
|---|---|---|
| EP | 0 408 198 A1 | 1/1991 |
| EP | 0 427 429 A2 | 5/1991 |
| EP | 0 917 886 A1 | 5/1999 |
| EP | 1 234 594 A2 | 8/2002 |
| GB | 2 209 121 A | 5/1989 |
| WO | WO 93/17750 A1 | 9/1993 |

\* cited by examiner

OCCLUSION BALLOON CATHETER WITH EXTERNAL INFLATION LUMEN

TECHNICAL FIELD

The invention relates generally to catheters and more specifically to balloon catheters that include external inflation means.

BACKGROUND OF THE INVENTION

Catheters such as guide catheters can be subject to a number of often conflicting performance requirements such as flexibility, strength, minimized exterior diameter, maximized interior diameter, and the like. In particular, there can be a balance between a need for flexibility and a need for strength or column support. If a catheter is sufficiently flexible to reach and pass through tortuous vasculature, the catheter may lack sufficient column strength to remain in position while, for example, subsequent treatment devices are advanced through the catheter.

Some medical procedures require a method of occluding blood flow distally of a treatment site, while other procedures benefit from occluding blood flow proximally of a treatment site. While a balloon catheter can be used to occlude blood flow, inclusion of a balloon catheter requires either a separate inflation lumen through a guide catheter or a substantial amount of the lumen space within the guide catheter devoted to inflation.

A need remains for a catheter such as a guide catheter that can provide desired strength versus flexibility characteristics. A need remains for a catheter such as a guide catheter that can occlude blood flow without sacrificing the interior lumen space otherwise required by a conventional balloon catheter.

SUMMARY OF THE INVENTION

The invention is directed to catheters such as balloon guide catheters configured for providing proximal occlusion, while still providing sufficient interior lumen space for device delivery. The invention is directed to catheters such as guide catheters that also provide a desired level of flexibility, yet can include sufficient column support.

Accordingly, one embodiment of the invention is a catheter with distal and proximal regions, an elongate shaft extending between the distal and proximal regions defining a lumen therebetween, an inflatable, preferably, compliant balloon attached to the distal region of the elongate shaft, and an external inflation component. The inflation component has an inflation lumen in fluid communication with the interior of the balloon. The inflation component is disposed longitudinally along the outer surface of the elongate shaft.

BRIEF DESCRIPTION OF THE DRAWINGS

The invention may be more completely understood in consideration of the following detailed description of various embodiments of the invention in connection with the accompanying drawings, in which.

DETAILED DESCRIPTION OF PREFERRED EMBODIMENTS

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The drawings, which are not necessarily to scale, depict illustrative embodiments of the claimed invention.

Figure 1:
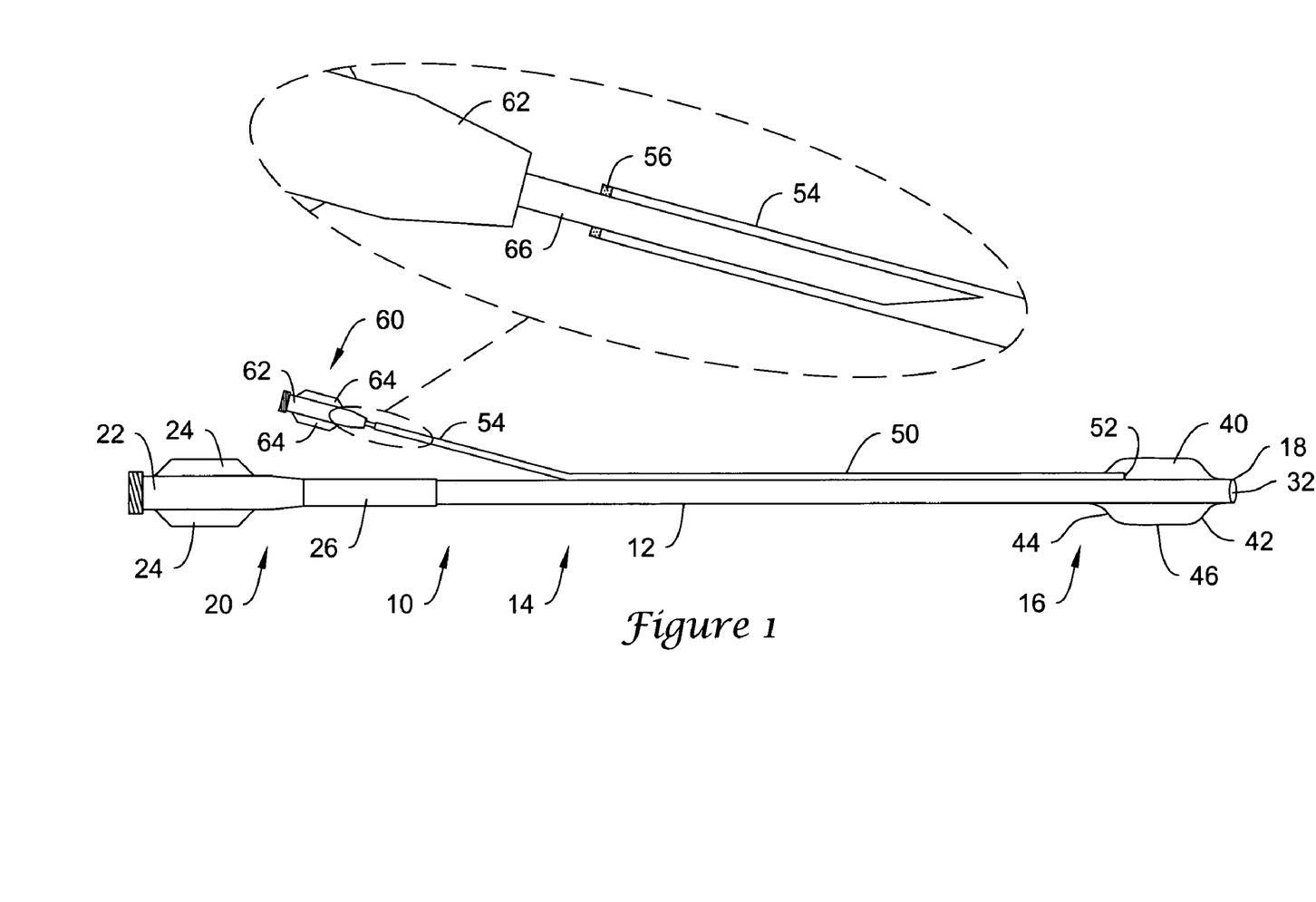
FIG. 1 is a side elevation view of a balloon catheter in accordance with an embodiment of the invention.

FIG. 1 is a plan view of a catheter 10 in accordance with an embodiment of the invention. The catheter 10 can be one of a variety of different catheters, but is preferably an intravascular catheter. Examples of intravascular catheters include balloon catheters, atherectomy catheters, drug delivery catheters, diagnostic catheters and guide catheters. As illustrated, FIG. 1 portrays a guide catheter, but the invention is not limited to such. Except as described herein, the intravascular catheter 10 can be manufactured using conventional techniques and materials.

The intravascular catheter 10 can be sized in accordance with its intended use. The catheter 10 can have a length that is in the range of about 50 centimeters to about 110 centimeters and can have a diameter that is in the range of about 4F (French) to about 9F.

In the illustrated embodiment, the intravascular catheter 10 includes an elongate shaft 12 that has a proximal region 14, a distal region 16 and a distal end 18. Shaft 12 defines a working lumen 32 extending from the proximal region 14 to the distal end 18. A hub and strain relief assembly 20 can be connected to the proximal region 14 of the elongate shaft 12. The hub and strain relief assembly 20 can be of conventional design and can be attached using conventional techniques.

In one embodiment, the hub and strain relief assembly 20 includes a main hub body portion 22, a pair of flanges 24 designed to improve gripping, and a strain relief 26. The strain relief 26 spans the connection between the proximal end 14 of the shaft 12 and the hub 22 to reduce the tendency of the shaft 12 to kink therebetween. The hub 22 can be made of clear polycarbonate, and the strain relief 26 can be made of polyether-ester. The hub 22 can be adhesively secured to the proximal end 14 of the shaft 12 and the strain relief 26 utilizing an ultraviolet (UV) curable adhesive.

Catheter 10 includes a balloon 40 having a distal portion 42, an intermediate portion 46, and proximal portion 44. The balloon 40 is disposed about the distal region 16 of the shaft 12, proximal to the distal end 18. In a preferred embodiment, the balloon 40 is a compliant inflatable membrane with elastomeric properties. The balloon 40 can be formed of a urethane polymer or a thermoplastic rubber elastomer, such as Chronoprene™, available from Carditech International, Inc. The balloon 40 is expandable between a collapsed configuration and an inflated configuration. Upon inflation, the balloon 40 conforms to the shape of the interior of the body lumen in which the catheter 10 is disposed, such as a blood vessel. In the collapsed configuration (not shown), the balloon 40 has the same general diameter as the distal end of the shaft 12. This allows the catheter 10 to be maneuvered easier and into smaller vessels than catheters having conventional fixed-sized, folded balloons.

The balloon 40 can be sized as appropriate to fit over the elongate shaft 12, as well as to nearly or completely occlude a particular vasculature in which the balloon 40 will be used. In some embodiments, the balloon 40 can have a length that is in the range of about 0.5 cm to about 2 cm. The balloon 40 can have a first diameter (collapsed configuration) that is in the range of about 0.065 inches to about 0.13 inches and a second diameter (expanded configuration) that is in the range of about 1 mm to about 1.5 cm.

The compliant inflatable balloon 40 can be inflated to various diameters, depending on the volume of inflation fluid inserted into the balloon 40. This allows a single size catheter 10 to be used in a variety of different sized body vessels. In order to facilitate inflation to a desired balloon diameter and avoid over-inflation, a chart can be provided listing various balloon diameters and the volume of inflation fluid generally required to achieve each diameter.

Figure 2:
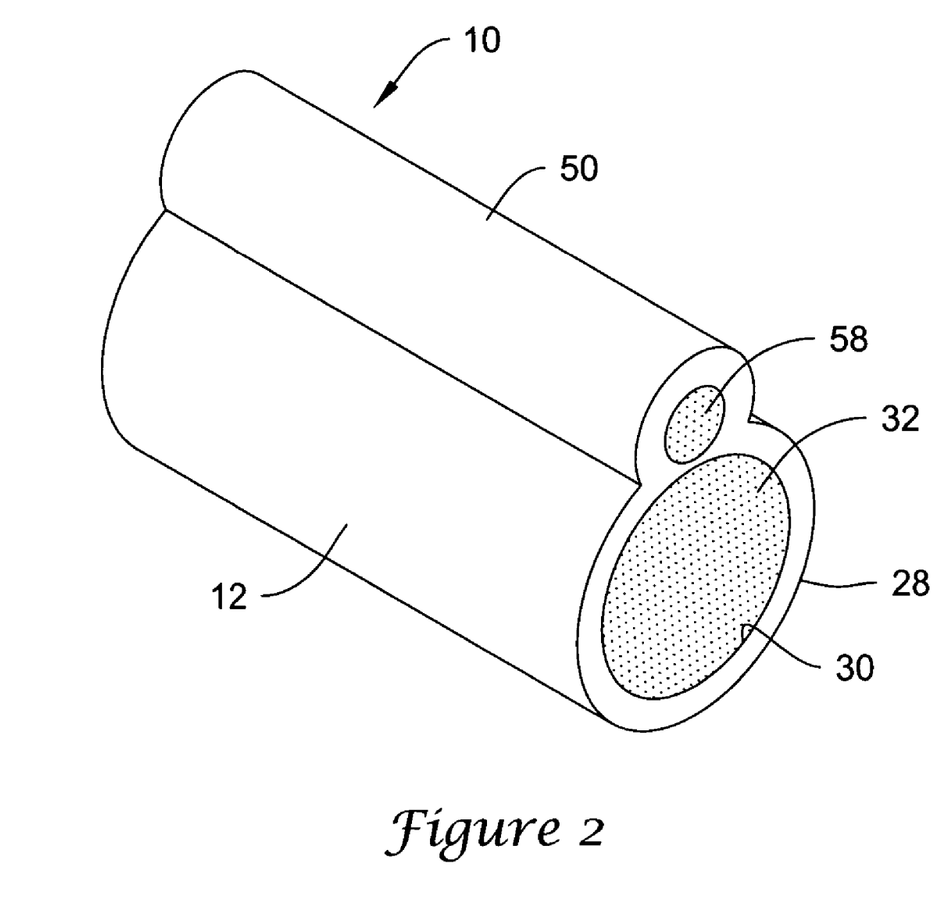
FIG. 2 is a perspective view of a portion of the catheter shaft of FIG. 1.

The compliant balloon 40 is inflated via an external inflation component 50 that is disposed adjacent the shaft 12 at least along the distal region 16. As illustrated in FIGS. 1 and 2, the external inflation component 50 extends longitudinally along the external surface 28 of the shaft 12. The external inflation component 50 defines an inflation lumen 58 and has a distal end 52 in fluid communication with the interior of the balloon 40, and a proximal end 54 with a sealing member 56.

The distal portion 42 of the balloon 40 is attached to the distal region 16 of the shaft 12, and the proximal portion 44 of the balloon 40 is attached proximally over both the shaft 12 and the distal end 52 of the external inflation component 50, such that the inflation lumen 58 of the inflation component 50 is in fluid communication with an interior of the balloon 40. When an inflation fluid is inserted through the external inflation component 50 into the balloon 40, at least the intermediate portion 46 of the balloon 40 moves radially outward, as shown in FIG. 1. In one embodiment, the distal end 18 of the shaft 12 extends distally of the balloon 40.

The external inflation component 50 can have a hub assembly 60 for connecting to an inflation source. The hub assembly 60 can include a main body portion 62, a pair of flanges 64 designed to improve gripping, and a connection member 66 for connecting an inflation source to the inflation lumen 58 of the external inflation component 50. In one embodiment, the hub assembly 60 can be a hypodermic needle, with the needle as the connection member 66 being inserted through the sealing member 56 into the inflation lumen 58. The sealing member 56 can be any means of sealing the inflation component 50 around the connection member 66, including a valve, threaded connector, or compression fitting.

FIG. 2 is a perspective view of the catheter 10 illustrating the relationship between the elongate shaft 12 and external inflation component 50. The external inflation component 50 is attached to the shaft 12 such that the working lumen 32 and inflation lumen 58 are substantially parallel. The external inflation component 50 may be attached to the shaft 12 by shrinking a thin wall of polymer material over the shaft 12 and external inflation component 50. An example of a suitable polymer is a polyether block co-polyamide polymer such as PEBAX®. In another embodiment, the external inflation component 50 can be attached to the shaft 12 by heating and fusing or with an adhesive such as a UV curable adhesive.

The external inflation component 50 can be formed of materials such as metals, metal alloys, polymers, metal-polymer composites, or other suitable materials. Some examples of some suitable materials can include stainless steels (e.g., 304v stainless steel), nickel-titanium alloys (e.g., nitinol, such as super elastic or linear elastic nitinol), nickel-chromium alloys, nickel-chromium-iron alloys, cobalt alloys, nickel, titanium, platinum, or alternatively, a polymer material such as a high performance polymer, or other suitable materials, and the like.

In some embodiments, the external inflation component 50 can be formed of a shape memory material such as a nickel-titanium alloy. Nitinol is an exemplary shape memory material. Within the family of commercially available nitinol alloy is a category designated "linear elastic" which, although similar in chemistry to conventional shape memory and superelastic varieties, exhibits distinct and useful mechanical properties. By skilled applications of cold work, directional stress, and heat treatment, the tube is fabricated in such a way that it does not display a substantial "superelastic plateau" or "flag region" in its stress/strain curve. Instead, as recoverable strain increases, the stress continues to increase in an essentially linear relationship until plastic deformation begins. In some embodiments, the linear elastic nickel-titanium alloy is an alloy that does not show any martensite/austenite phase changes that are detectable by DSC and DMTA analysis over a large temperature range.

For example, in some embodiments, there is no martensite/austenite phase changes detectable by DSC and DMTA analysis in the range of about −60° C. to about 120° C. The mechanical bending properties of such material are, therefore, generally inert to the effect of temperature over this very broad range of temperature. In some particular embodiments, the mechanical properties of the alloy at ambient or room temperature are substantially the same as the mechanical properties at body temperature.

In some embodiments, the linear elastic nickel-titanium alloy is in the range of about 50 to about 60 weight percent nickel, with the remainder being essentially titanium. In some particular embodiments, the composition is in the range of about 54 to about 57 weight percent nickel. One example of a suitable nickel-titanium alloy is FHP-NT alloy commercially available from Furukawa Techno Material Co., of Kanagawa, Japan. Some examples of nickel-titanium alloys include those disclosed in U.S. Pat. Nos. 5,238,004 and 6,508,803, which are incorporated herein by reference.

Examples of polymers from which the external inflation component 50 can be made include polyether block co-polyamide polymers, polypropylene, polyethylene (PE) or other conventional polymers used in making catheters. The proximal end 54, distal end 52 and central portion of the inflation component 50 can be made of different polymers and/or metals with varying stiffness. The inflation component 50 can be a hypotube. In one embodiment, the inflation component 50 is a nitinol hypotube with polymer tubing at the distal end. This configuration provides for greater strength and flexibility. In another embodiment, the inflation component 50 is a polymer tube reinforced with a metal braid, coil or ribbon.

The metal reinforcement can be platinum, stainless steel, nitinol, or other suitable metal.

In some embodiments, the majority of the length of the shaft 12 includes a reinforcing braid or ribbon layer to increase particular properties such as kink resistance. The shaft 12 can be made of discrete tubular layers. In one embodiment, the inner surface 30 of shaft 12 is a lubricious layer and the outer surface 28 is a polymer layer. A metallic reinforcement layer such as a braid, coil, or ribbon can be disposed between the inner surface 30 and the outer surface 28 of the shaft 12. The inner lubricious surface can be formed of a prefabricated polytetrafluoroethylene (PTFE) tube.

In other embodiments (not illustrated), the outer surface 28 can include multiple discrete axial sections generally increasing in flexibility from the proximal region 14 of the shaft 12 to the distal end 18 of the shaft 12. The number of discrete sections can be two, three, four, five, or more. In one embodiment, the outer surface 28 includes five sections. The inner lubricious surface extends through outer sections one through four and a substantial portion of outer section five. Similarly, the reinforcement layer extends through outer tube sections one through four and a portion of outer tube section five. In one embodiment, outer tube sections one through five have a length of about 86.0 cm, about 21.5 cm, about 0.5-2.0 cm, about 1.0-6.8 cm, and about 0.36 cm, respectively. The fifth outer tube section can include a tip portion having a length of approximately 0.13 cm that is free of the lubricious surface and the braided reinforcement layer. In some embodiments, the elongate shaft 12 can also include a distal tip segment that can be formed from a softer, more flexible polymer.

If the elongate shaft 12 has, for example, three segments, such as a proximal segment, an intermediate segment and a distal segment, each segment can include an inner surface 30 that is the same for each segment and an outer surface 28 that becomes increasingly more flexible with proximity to the distal end 18 of the elongate shaft 12. For example, the proximal segment can have an outer surface that is formed from a polymer having a hardness of 72 D (Durometer), the intermediate segment can have an outer surface that is formed from a polymer having a hardness of 68 D and the distal segment can be formed from a polymer having a hardness of 46 D.

If the elongate shaft 12 has three segments, each of the segments can be sized in accordance with the intended function of the resulting catheter 10. For example, the proximal segment can have a length of about 35 inches, the intermediate segment can have a length that is in the range of about 2 inches to about 3 inches, and the distal segment can have a length that is in the range of about 1 inch to about 1.25 inches.

The inner surface 30 can be a uniform material and can define a working lumen 32 that can run the entire length of the elongate shaft 12 and that is in fluid communication with a lumen (not illustrated) extending through the hub assembly 20. The working lumen 32 defined by the inner surface 30 can provide passage to a variety of different medical devices, and thus, the inner surface 30 can include, be formed from or coated with a lubricious material to reduce friction within the working lumen 32. An exemplary material is polytetrafluoroethylene (PTFE), better known as TEFLON®. The inner surface 30 can be dimensioned to define a working lumen 32 having an appropriate inner diameter to accommodate its intended use. In some embodiments, the inner surface 30 can define a working lumen 32 having a diameter of about 0.058 inches and the inner surface 30 can have a wall thickness of about 0.001 inches.

The outer surface 28 can be formed from any suitable polymer that will provide the desired strength, flexibility or other desired characteristics. Polymers with low durometer or hardness can provide increased flexibility, while polymers with high durometer or hardness can provide increased stiffness. In some embodiments, the polymer material used is a thermoplastic polymer material. Some examples of some suitable materials include polyurethane, elastomeric polyamides, block polyamide/ethers (such as PEBAX®), silicones, and co-polymers. The outer surface 28 can be a single polymer, multiple layers, or a blend of polymers. By employing careful selection of materials and processing techniques, thermoplastic, solvent soluble, and thermosetting variants of these materials can be employed to achieve the desired results.

In particular embodiments, a thermoplastic polymer such as a co-polyester thermoplastic elastomer such as that available commercially under the ARNITEL® name can be used. The outer surface 28 can have an inner diameter that is about equal to the outer diameter of the inner surface 30.

Depending on the size of the catheter 10, the outer surface 28 can have an inner diameter in the range of about 0.0600 inches to about 0.0990 inches. For example, shafts of sizes 6French (6F), 7F, 8F, and 9F can have inner diameters of 0.064 inches, 0.073 inches, 0.086 inches, and 0.099 inches, respectively. The outer diameter can be in the range of about 0.0675 inches to about 0.118 inches, with 0.079 inches, 0.092 inches, 0.105 inches, and 0.118 inches, respectively, for 6F, 7F, 8F, and 9F. Part or all of the outer surface 28 can include materials added to increase the radiopacity of the outer surface 28, such as 50% bismuth subcarbonate.

Figure 3:
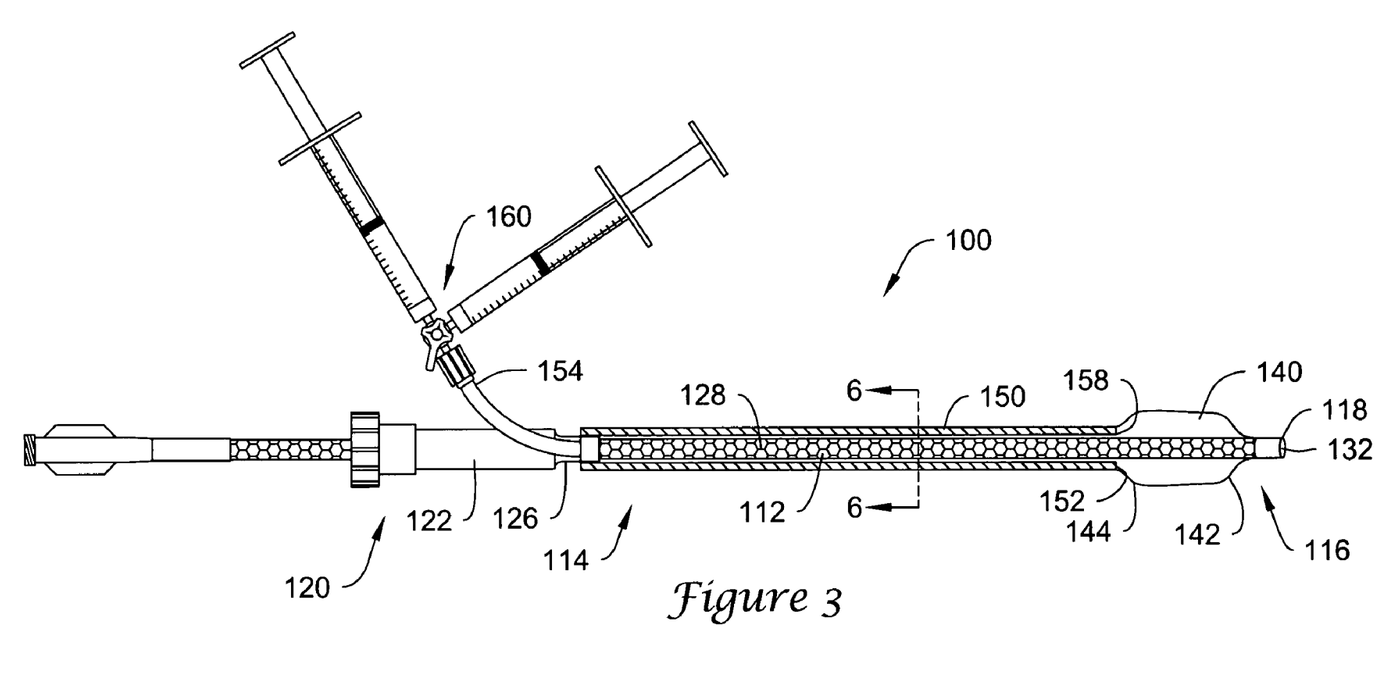
FIG. 3 is a partially sectioned view of a balloon catheter in accordance with another embodiment of the invention.

FIG. 3 illustrates an embodiment in which the catheter 100 has an elongate shaft 112 with a working lumen 132 and a compliant inflatable balloon 140 attached to a distal region 116 of the shaft 112. The catheter has an external inflation component 150 extending from a proximal region 114 of the shaft 112 to proximal of the distal end 118 of the shaft 112. The distal end 142 of the balloon 140 is attached to the outer surface 128 of the shaft 112 proximally of the distal end 118, and the proximal end 144 of the balloon 140 is attached to the distal end 152 of the inflation component 150.

The external inflation component 150 is a sleeve disposed about the outer surface 128 of the shaft 112. The outer diameter of the shaft 112 is slightly smaller than the inner diameter of the inflation component 150 such that an annular inflation lumen 158 is defined. The distal end of the inflation lumen 158 is in fluid communication with the interior of the balloon 140. The proximal end of the inflation lumen 158 is in fluid communication with an inflation fluid source. In the embodiment illustrated in FIG. 3, the proximal end 154 of the inflation component 150 has a connection member 160 such as a hub or valve system for controlling the insertion and withdrawal of inflation fluid.

Figure 4:
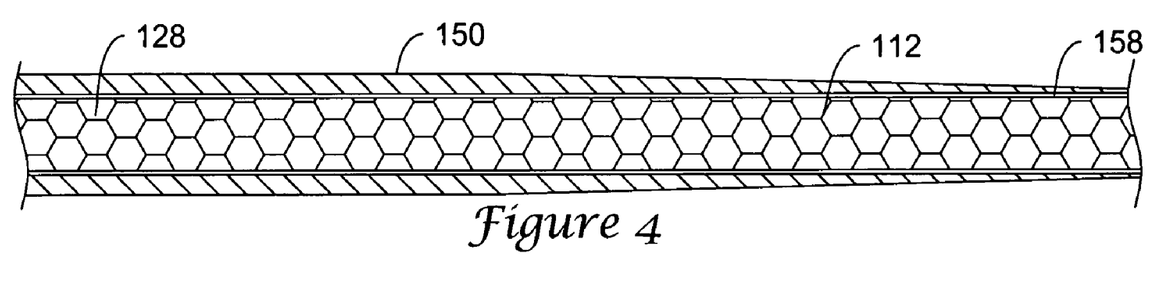
FIGS. 4 and 5 are partially sectioned views of the distal region of a catheter according to an embodiment of the invention.
Figure 5:
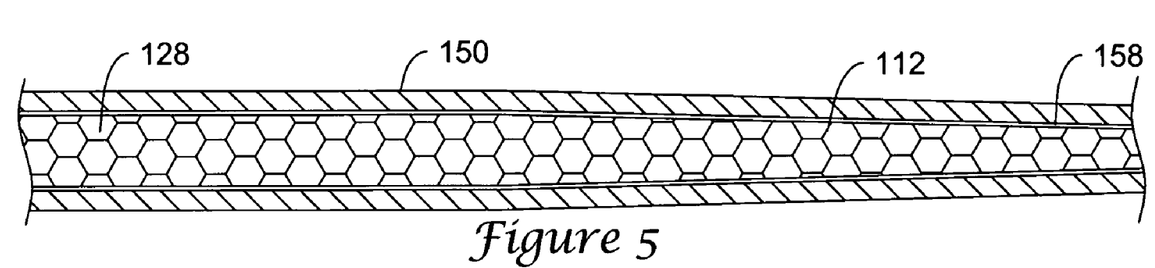

The distal region of the catheter 100 can be tapered. In one embodiment as shown in FIG. 4, the diameter of the shaft 112 and inflation lumen 158 remains constant throughout the length of the shaft 112, while the outer wall of the inflation component 150 is tapered toward the distal end. FIG. 5 illustrates another embodiment in which the shaft 112 is tapered, while the inflation lumen 158 and the outer wall of the inflation component 150 remains constant. In both embodiments, the overall diameter of the catheter 100 tapers toward the distal end, while the diameter of the inflation lumen 158 remains constant. The embodiment of FIG. 4 provides a constant working lumen diameter and can provide increased flexibility at the distal end due to the reduced outer wall thickness. The embodiment of FIG. 5 can provide greater strength at the distal end due to the constant outer wall thickness.

Figure 6:
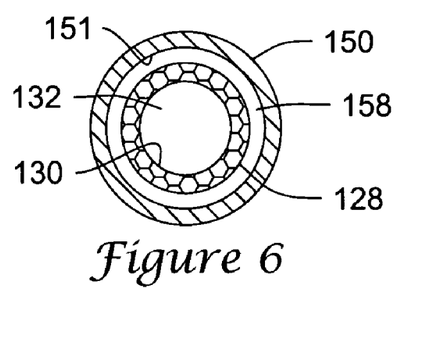
FIG. 6 is a cross-section taken along line 6-6 of FIG. 3.

As illustrated, for example, in FIG. 6, which is a cross-section taken along line 6-6 of FIG. 3, the inflation component 150 can be a single layer having an inflation lumen 158 therethrough that is sized to accommodate the outer surface 128 of the elongate shaft 112. In some embodiments, the inflation component 150 can have an outer diameter that is in the range of about 0.065 inches to about 0.13 inches and an inner diameter that is in the range of about 0.050 inches to about 0.12 inches. The inflation component 150 can have an overall length that is in the range of about 50 cm to about 150 cm.

The single layer inflation component 150 has an outer surface and an inner surface 151. The inflation component 150 can be formed of any suitable material such as a polymeric material. Polymers with low durometer or hardness can provide increased flexibility, while polymers with high durometer or hardness can provide increased stiffness. In some embodiments, the inflation component 150 can be formed of a material that will provide the inflation component 150 with characteristics useful in providing column support to the elongate shaft 112 when the inflation component 150 is deployed thereon.

In some embodiments, the polymer material used is a thermoplastic polymer material. Some examples of some suitable materials include those discussed previously with respect to the outer surface 28 of the elongate shaft 12. By employing careful selection of materials and processing techniques, thermoplastic, solvent soluble, and thermosetting variants of these materials can be employed to achieve the desired results.

In the illustrated embodiment in which the inflation component 150 is a single layer, its inner surface 151 can be coated with a lubricious material to reduce friction between the inner surface 151 and the outer surface 128 of the elongate shaft 112. An exemplary material is polytetrafluoroethylene (PTFE), better known as TEFLON®. The inner surface 130 of the elongate shaft 112 can also be coated with a lubricious material to reduce friction between the inner surface 130 and devices passing through the lumen 132.

In some embodiments (not illustrated), the inflation component 150 can be formed having two or more layers. In such embodiments, the inflation component 150 can have an inner layer that includes, is coated with, or formed from TEFLON®. The outer layer can be formed of any suitable polymer such as those discussed with respect to the outer layer 128 of the elongate shaft 112. The shaft can also be formed of two or more layers including polymers and reinforcing braid, coil, or ribbon.

As discussed previously, the catheter assembly 100 includes an elongate shaft 112 which extends through the inflation component 150 and balloon 140. As illustrated in FIG. 3, the catheter assembly 100 can include a proximal hub 120 having a hub body 122 that can be configured to easily permit insertion of the elongate shaft 112 therethrough. The catheter assembly 100 can also include a hub assembly 160 disposed at the proximal end 154 of the inflation component 150. The hub assembly 160 can provide connections for attaching means for injecting and withdrawing inflation fluid.

In use, the catheter 10, 100 is inserted into a body lumen such as a blood vessel, until the balloon 40, 140 is positioned proximal, or upstream, of the treatment site. Inflation fluid is inserted through the external inflation component 50, 150 and into the balloon 40, 140. Inflation of the balloon 40, 140 results in occlusion of the vessel, allowing the physician to perform the necessary treatment at the distal treatment site without blood flowing through the vessel. This arresting of blood flow is particularly important for permitting retrieval of foreign body materials or clots without the risk of them being carried distally due to blood flow pressure. Placement of a treatment device that extends distally beyond the distal end 18, 118 of the elongate shaft 12, 112 prior to expanding the balloon 40, 140 can minimize the amount of time over which blood flow is occluded.

In some embodiments, parts of the catheter assembly 10, 100 can be made of, include, be doped with, include a layer of, or otherwise include a radiopaque material. Radiopaque materials are understood to be materials capable of producing a relatively bright image on a fluoroscopy screen or another imaging technique during a medical procedure. This relatively bright image aids the user of device in determining its location. Some examples of radiopaque materials can include, but are not limited to, gold, platinum, palladium, tantalum, tungsten alloy, plastic material loaded with a radiopaque filler, and the like.

In some embodiments, a degree of MRI compatibility can be imparted. For example, to enhance compatibility with Magnetic Resonance Imaging (MRI) machines, it may be desirable to make any metallic parts in a manner that would impart a degree of MRI compatibility. For example, if a metallic reinforcement structure such as a braid, coil, or ribbon is included in the catheter, the reinforcement structure can be made of a material that does not substantially distort the image and create substantial artifacts (artifacts are gaps in the image). Certain ferromagnetic materials, for example, may not be suitable because they may create artifacts in an MRI image. Any metallic reinforcement structures can also be made from a material that the MRI machine can image. Some materials that exhibit these characteristics include, for example, tungsten, Elgiloy, MP35N, nitinol, and the like.

In some embodiments, part or all of the catheter assembly 10, 100 can include a lubricious coating. Lubricious coatings can improve steerability and improve lesion crossing capability. Examples of suitable lubricious polymers include hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers can be blended among themselves or with formulated amounts of water insoluble compounds (including some polymers) to yield coatings with suitable lubricity, bonding and solubility. In some embodiments, a distal portion of the catheter can be coated with a hydrophilic polymer, while the more proximal portions can be coated with a fluoropolymer.

It should be understood that this disclosure is, in many respects, only illustrative. Changes may be made in details, particularly in matters of shape, size and arrangement of steps, without exceeding the scope of the invention. The invention's scope is, of course, defined in the language in which the appended claims are expressed.

What we claim is:

1. A balloon catheter having a distal region and a proximal region, the balloon catheter comprising:
    an elongate shaft extending from the distal region to the proximal region and defining a working lumen therebetween, the elongate shaft having a distal end, an inner surface and an outer surface;
    an inflatable compliant balloon disposed about a portion of the distal end of the outer surface of the elongate shaft such that the shaft extends through the balloon; and
    an external inflation component comprising a sleeve having an annular wall having an inner surface and an outer surface, wherein the radial distance between the inner surface of the sleeve and the outer surface of the sleeve defines a thickness of the annular wall;

wherein the sleeve is disposed longitudinally about the outer surface of the elongate shaft extending from the proximal region of the shaft to proximal of the distal end of the shaft, wherein the inner surface of the sleeve is spaced from the outer surface of the shaft, creating an annular inflation lumen in fluid communication with the balloon;

wherein the thickness of the annular wall of the sleeve tapers toward the distal end of the shaft throughout a length of the shaft while the radial distance between the outer surface of the shaft and the inner surface of the sleeve remains constant throughout the length of the shaft in which the thickness of the annular wall tapers, resulting in a catheter with a tapered distal region.

2. The catheter of claim 1, wherein a distal end of the balloon is attached to the distal end of the shaft and a proximal end of the balloon is attached to a distal end of the sleeve.

3. The catheter of claim 2, wherein the sleeve is a single layer polymer, the sleeve being attached to an inflation hub at a proximal end of the sleeve.

4. The catheter of claim 1, wherein the annular inflation lumen has a diameter of about 0.002 inches at the distal end of the sleeve.

5. The catheter of claim 1, wherein the annular inflation lumen has a diameter of about 0.004 inches at a proximal end of the sleeve.

6. A balloon catheter having a distal region and a proximal region, the balloon catheter comprising:

an elongate shaft extending from the distal region to the proximal region and defining a working lumen therebetween, the elongate shaft having a distal end, an inner surface and an outer surface;

an inflatable compliant balloon disposed about a portion of the distal end of the outer surface of the elongate shaft such that the shaft extends through the balloon; and an external inflation component comprising a sleeve having an annular wall having an inner surface and an outer surface, wherein the radial distance between the inner surface of the sleeve and the outer surface of the sleeve defines a thickness of the annular wall;

wherein the sleeve is disposed longitudinally about the outer surface of the elongate shaft extending from the proximal region of the shaft to proximal of the distal end of the shaft, wherein the inner surface of the sleeve is spaced from the outer surface of the shaft, creating an annular inflation lumen in fluid communication with the balloon;

wherein both the outer surface of the sleeve and the outer surface of the shaft taper toward the distal end of the shaft throughout a length of the shaft while the radial distance between the outer surface of the shaft and the inner surface of the sleeve remains constant throughout the length of the shaft in which the outer surface of the sleeve and the outer surface of the shaft tapers, resulting in a catheter with a tapered distal region.

* * * * *